(12) United States Patent
King (10) Patent No.: US 6,210,566 B1
(45) Date of Patent: *Apr. 3, 2001

(54) NESTABLE CONTAINERS AND IMPROVED WATER TREATMENT MATERIALS

(76) Inventor: Joseph A. King, 16261 S. Temple Dr., Minnetonka, MN (US) 55343

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/719,482

(22) Filed: Sep. 25, 1996

(51) Int. Cl.$^7$ ....................................... E04H 4/12
(52) U.S. Cl. ................. 210/169; 210/754; 210/205; 210/256; 424/661; 424/641; 424/618; 137/268; 422/190; 422/236; 422/261; 422/283
(58) Field of Search .................... 424/618, 619, 424/600, 641, 661–665; 137/268; 422/188–190, 236, 261, 283; 210/253, 255, 256, 198.1, 754, 755, 756, 205, 206, 169

(56) References Cited

U.S. PATENT DOCUMENTS

| | | | |
|---|---|---|---|
| 1,260,777 | 3/1918 | Kirkegaard | 422/278 |
| 2,017,456 | 10/1935 | Gudmundsen | 210/105 |
| 3,378,027 | 4/1968 | Fredericks et al. | 137/268 |
| 3,595,395 | 7/1971 | Lorenzen | 210/169 |
| 3,746,170 | 7/1973 | Bloom et al. | 210/198 |
| 3,899,425 | 8/1975 | Lewis | 210/206 |
| 4,092,245 | 5/1978 | Franks et al. | 210/64 |
| 4,178,690 | * 12/1979 | Aine . | |
| 4,249,562 | 2/1981 | King, Sr. | 137/268 |
| 4,270,565 | 6/1981 | King, Sr. | 137/268 |
| 4,331,174 | 5/1982 | King, Sr. | 137/268 |
| 4,407,865 | 10/1983 | Nice | 427/217 |
| 4,420,394 | 12/1983 | Lewis | 210/169 |
| 4,481,110 | 11/1984 | Shannon | 210/199 |
| 4,504,387 | 3/1985 | LeMire et al. | 210/101 |
| 4,608,247 | 8/1986 | Heinig, Jr. | 424/16 |
| 4,610,783 | 9/1986 | Hudson | 210/169 |
| 4,642,192 | 2/1987 | Heskett | 210/638 |
| 4,662,387 | 5/1987 | King, Sr. | 137/268 |
| 4,780,197 | 10/1988 | Schuman | 210/136 |
| 4,790,981 | 12/1988 | Mayer et al. | 422/263 |
| 4,867,196 | 9/1989 | Zetena et al. | 137/268 |
| 4,935,116 | 6/1990 | LeMire | 204/237 |
| 4,964,185 | 10/1990 | Lehn | 8/158 |
| 5,041,219 | 8/1991 | Strand et al. | 210/284 |

(List continued on next page.)

FOREIGN PATENT DOCUMENTS 2215325 9/1989 (GB) .
WO 96/14093 5/1996 (WO) .

OTHER PUBLICATIONS www.kingtechnology.com/company.htm downloaded Feb. 19, 2000.*
Chemical Abstracts 87: 172677P (1977).*
Chemical Abstracts 87: 156914h (1977).*

(List continued on next page.)

Primary Examiner—David A. Simmons
Assistant Examiner—Chester T. Barry
(74) Attorney, Agent, or Firm—Jacobson & Johnson (57) ABSTRACT

Nestable canisters for use in a dispersal valve that normally holds only a single canister with the nestable canisters suitable for replacing single canisters to enable a fluid mixing stream to be bifurcated and simultaneously but separately treat the water with different materials. The fluid mixing stream which normally flows through the set of ports that are used for dispensing only one solid chemical into the liquid stream flowing through the dispersal valve is bifurcated to provide for both dispersant type bacteria killing as well as in situ bacteria killing. In addition the nestable canisters are provided with an improved bactericide and algaecide for killing algae in the water and absorbing acids that might be generated by use of chlorine in the dispersal valve.

16 Claims, 7 Drawing Sheets

U.S. PATENT DOCUMENTS

| | | | |
|---|---|---|---|
| 5,053,206 | 10/1991 | Maglio et al. | 422/264 |
| 5,076,315 | 12/1991 | King | 137/268 |
| 5,124,032 * | 6/1992 | Newhard | 210/169 |
| 5,171,687 | 12/1992 | Moller et al. | 435/286 |
| 5,190,651 * | 3/1993 | Spencer et al. . | |
| 5,201,339 | 4/1993 | Buchan et al. | 137/268 |
| 5,218,983 | 6/1993 | King | 137/1 |
| 5,234,588 | 8/1993 | Aymes | 210/202 |
| 5,251,656 | 10/1993 | Sexton, Sr. | 137/1 |
| 5,350,512 | 9/1994 | Tang | 210/199 |
| 5,352,369 | 10/1994 | Heinig, Jr. | 210/760 |
| 5,407,567 | 4/1995 | Newhard | 210/198.1 |
| 5,413,706 | 5/1995 | Graves | 210/110 |
| 5,426,899 * | 6/1995 | Jones . | |
| 5,447,641 | 9/1995 | Wittig | 210/756 |
| 5,498,333 | 3/1996 | Canther | 210/198 |
| 5,503,840 * | 4/1996 | Jacobson . | |
| 5,507,945 | 4/1996 | Hansen | 210/198.1 |
| 5,584,991 * | 12/1996 | Wittstock . | |
| 5,656,159 * | 8/1997 | Spencer et al. . | |
| 5,772,896 * | 6/1998 | Denkewicz, Jr. et al. | 210/754 |
| 5,855,777 * | 1/1999 | Bachand et al. | 210/205 |

OTHER PUBLICATIONS

Data Base WPI Section Ch, Week 9544 Derwent Publications Ltd., London, GB; class A23, AN 95–34048 XP 002078711 & Patent abstracts of Japan vol. 096, No. 001, Jan. 31, 1996& JP 07 233017 A (Satosen Co Ltd). Sep. 5, 1995.

European Search Report EP 97 11 6259 (2 Pages—Double Sided), Sep. 1998.

European Patent Office—Patent Abstracts of Japan—Publication #6048909—Title "Algae–Proofing Composition and Algae–Proofing Agent for Aquarium Fish Using the Composition". (Feb. 1994).

* cited by examiner

NESTABLE CONTAINERS AND IMPROVED WATER TREATMENT MATERIALS

FIELD OF THE INVENTION

This invention relates in general to nestable canisters and an improved bactericide/algaecide for use in water treatment and more particularly to nestable canisters that can be inserted into a dispenser that normally holds a single canister to provide for simultaneous but separate dispensing of dispersants and minerals to kill both bacteria and algae in recirculating water systems commonly used in swimming pools, spas and the like.

BACKGROUND OF THE INVENTION

The concept of treating water with chemicals such as chlorine or bromine to kill bacteria is old in the art. One of the methods of dispensing bacteria killing chemicals into the water is to use a dispersal valve that allows a portion of the water to flow through the water soluble chemical which is located in a single compartment within the dispersal valve. Typically, a chemical such as chlorine or a metallic compound such as silver is used to kill the bacteria.

The prior art further includes devices that hold two solids and separately dispenses the dissolvable solids into the water as shown in the U.S. Pat. No. 3,378,027. The patent shows a water treatment apparatus having two separate compartments each for holding a dissolvable solid chemical therein. Once the chemicals are dissolved they are allowed to flow into a storage tank.

Still another apparatus for dispensing two different chemicals is shown in U.S. Pat. No. 5,251,656 which shows a multiple chemical feeder for swimming pools. The feeder has a first compartment for holding a canister containing a solid chemical and a second compartment for holding a collapsible container having a liquid chemical dispersant. The solid chemical is dissolved and dispensed by flowing water through it. The liquid chemical is dispensed by exerting pressure on the outside of a collapsible container to force the liquid chemical out of the dispenser and into the system. The chemicals are maintained separate from one another until they are introduced into the fluid stream. In the present invention the one portion of a bifurcated fluid stream flows through a canister holding a chemical dispersant and the other portion flows through a canister containing minerals which kill algae and bacteria to provide a system where the levels of the chemical dispersants can be maintained at a lower level without raising the level of bacteria in the system. After passing through the canisters the bifurcated stream is reunited and then directed into the liquid stream flowing through the dispersal valve.

The present invention allows one to use a prior art single compartment dispersal valve to hold nestable canisters wherein two different materials can be separately dissolved and simultaneously dispersed into a bifurcated fluid mixing stream with the bifurcated fluid mixing steam subsequently combined into a single stream for delivering the chemical and minerals dispersants into the liquid stream through a single dispersal valve. The nestable canisters are placeable within existing dispersal valves that normally contain only a single canister.

The nestable canisters provide for multiple water treatment in a single step by providing one canister that can dispense a dispersant such as chlorine and a second nestable canister that contains minerals such as an improved algaecide to provide both bacteria killing and algae killing capability from a dispersal valve that normally dispenses only a single dispersant at a time. The invention further includes an improved bactericide and algaecide comprising a zinc carrier having a silver coating which is located in an acid absorbing bed of limestone. The zinc and silver inhibit bacteria and algae while the limestone neutralizes acids formed during the water treatment process. The combination of the chemical treatment and the mineral treatment provides a treatment system that lowers the necessary amount of chemical in the pool as the bacteria is killed by contact with the minerals in the second canister.

BRIEF DESCRIPTION OF THE PRIOR ART

U.S. Pat. No. 3,378,027 shows a water treatment apparatus having two separate compartments each for holding a dissolvable chemical therein. Once the chemicals are dissolved with water the dissolvable chemicals are allowed to flow into a storage tank.

U.S. Pat. No. 4,504,387 shows a water purification system that uses charcoal granules impregnated with silver ions to kill bacteria.

U.S. Pat. No. 4,608,247 discloses a composition for bacterial treatment of water that uses a combination of a carrier with a layer of elemental silver on the carrier. The silver is released by the mechanical interaction of adjacent particles. The silver and carrier are located in a filler material that reduces the rate of release of the silver into the fluid stream.

U.S. Pat. No. 4,610,783 shows a system for the control of algae where the water is forced through staggered holes located in a set of zinc disks.

U.S. Pat. No. 4,642,192 shows a method for treating fluid to remove dissolved chlorine and nitrates by passing the water through a metal particulate matter such as aluminum, iron, steel, zinc, copper or mixtures and alloys thereof.

U.S. Pat. No. 4,662,387 discloses an in-line dispersal valve with a canister keyed to the dispersal valve.

U.S. Pat. No. 4,867,196 shows a dispenser with three chambers to obtain uniform and controlled release of the calcium hypochlorite.

U.S. Pat. No. 4,935,116 shows a canister that contains two dissimilar metals that are spaced from one another with one of the metals being silver to produce a simple voltaic cell that releases silver ions into the water as the water flows between the two dissimilar metals.

U.S. Pat. No. 4,964,185 shows a system for dispensing a chemical into a fluid stream and for determining how much of the chemical has been dispensed into the fluid stream.

U.S. Pat. No. 5,041,219 discloses a dual chamber water filter with a metallic filtration particulate located in the inlet chamber and a charcoal filtration particulate located in the outlet chamber with the metallic filtration particulate positioned so that water flows upward through it to reduce compaction of the metallic filtration particulate.

U.S. Pat. Nos. 5,218,983 and 5,076,315 to King disclose a dispersal valve with a canister for dispensing a water soluble chemical into a fluid stream.

U.S. Pat. No. 5,251,656 shows a multiple chemical feeder for swimming pools that has a first compartment for holding a canister containing a solid chemical and a second compartment containing a liquid chemical. The solid chemical is dissolved by flowing water through it. The liquid chemical is dispensed by exerting pressure on the outside of a collapsible container to force the liquid chemical out of the dispenser and into the system.

U.S. Pat. No. 5,352,369 discloses a method of treating water to kill bacteria using a silver catalyst which comprises an aluminum matrix with silver deposited thereon and the aluminum matrix and the silver having been heated between 750° C. and 1050° C.

U.S. Pat. No. 2,107,456 discloses a portable water treating system where a bed of germicidal filter material that has a activated carbon filter stacked on the germicidal filter material.

U.S. Pat. No. 4,092,245 shows a liquid purification system using a biocatalyst formed by wet processing silver oxide, zinc oxide and lampblack.

U.S. Pat. No. 4,407,865 discloses a process of coating a sterilizing filter material comprised of particulate silver material such as sand with metallic silver for sterilizing water.

BRIEF DESCRIPTION OF THE INVENTION

Briefly, the present invention comprises nestable canisters for use in dispersal valves that normally hold only a single canister with the nestable canisters suitable for replacing single canisters that disperse a chemical with a first canister to disperse a chemical dispersant and a second canister to bring the water in the valve into contact with bacteria killing minerals in the second canister. The dual canisters permit simultaneously but separate treatment of a temporarily bifurcated fluid mixing stream flowing through the set of dispersal valve ports that are normally used for dispensing only one chemical dispersant into a fluid mixing stream flowing through the dispersal valve. In addition the nestable canisters are provided with an improved bactericide and algaecide for killing bacteria and algae in the water.

BRIEF DESCRIPTION OF THE DRAWINGS

FIG. 1 is a pictorial view of a prior art dispersal valve;

FIG. 2 is a partial cut-away view of the dispersal valve of FIG. 1 with a single canister;

FIG. 3 is a perspective view of the canister for use in the dispersal shown in FIG. 1 and FIG. 2;

FIG. 4 is a perspective view of a first nestable canister for use in the dispersal valve of FIG. 1;

FIG. 4A is a bottom view of the nestable canister shown in FIG. 4;

FIG. 4B is a top view of the nestable canister shown in FIG. 4;

FIG. 5 is an exploded view of the nestable canister of FIG. 4 together with a manifold for connecting the nestable canister to a dispersal valve;

FIG. 5A is a top view of the manifold of FIG. 4;

FIG. 5B is front view of the manifold of FIG. 4;

FIG. 6 is a front view of a second nestable canister for nesting within the canister of FIG. 4;

FIG. 7 is a partial cut-away side view of a second nestable canister of FIG. 6;

FIG. 8 is an exploded perspective view showing the nesting relationship of the nestable canisters of FIG. 4 and FIG. 6;

FIG. 9 shows a partial cutaway view of a side elevation of a dispersal valve contain nestable canisters therein; and FIG. 10 shows a cross sectional view taken along lines 10—10 of FIG. 9 with the inner nestable canister removed for clarity.

FIG. 11 shows an alternate embodiment of the nestable canister.

DESCRIPTION OF THE PREFERRED EMBODIMENT

The present invention of nestable canisters for simultaneously but separately treating water in a temporarily bifurcated fluid mixing stream is usable in dispersal valves of the type normally used for dispensing a single chemical dispersant into pools, spas and the like.

FIG. 1 reference numeral 10 general identifies such a prior art dispersal valve for normally and controllable dispersing a single solid dispersant chemical such as bromine or chlorine tablets into a liquid. Dispersal valve 10 includes a housing 17 having a removable cover 11 fastened thereto by threads or the like. Located on top of cover 11 is an air vent 16 that can be opened to bleed air from dispersal valve 10. Located on top center of cover 11 is a visual indicator means 15 comprising an outer transparent, hollow sight member that permits an observer to peer through the sight member to determine if any visual indication means is present in the sight member.

Dispersal valve 10 which is shown in greater detail in my U.S. Pat. No. 5,076,315 includes a fluid inlet 13 on one side of housing 17 and a fluid outlet 12 located on the opposite side of housing 17. A rotary plug 14 permits a user to control the velocity of the fluid mixing stream that can be directed through the dispersal valve. A further example of a dispersal valve with a rotatable plug for controllably directing a fluid mixing stream through the dispersal valve to dispense materials such as bromine and chlorine into swimming pools, hot tubs, spas, and the like is shown in greater detail in U.S. Pat. No. 4,662,387. A beneficial feature of such a dispersal valve is that the mixing of the dispersant chemicals is done completely within the dispersant valve so that when the fluid mixing stream returns to the liquid stream through the dispersal valve the mixing stream can be further mixed with the liquid stream flowing through the dispersal valve thus assuring that higher concentrations of dispersant chemical are not directly introduced into the liquid stream which is returned to the pool or spa. That is, the dispersal valve ensures that the dispersant is always introduced in diluted form into the liquid stream so that the chances of human contact with high concentrations of dispersants in the pool or the spa is minimized.

FIG. 2 illustrates prior art valve 10 and a prior art canister 130 in cross section with chlorine tablets 9 located in a trough 153. The height of trough 153 is indicated by h and the liquid level in trough 153 is indicated by L. $P_2$ indicates the pressure at the inlet passage 151, $P_1$ indicates the pressure at the outlet 152 and $P_3$ indicates the pressure in the air pocket 150. In the embodiment shown the tablets in air pocket $P_3$ remain free of contact with liquid and remain in an undispensed state. However, the tablets 9 located in trough 153 are in contact with the liquid resulting in dispensing of dissolvable or errodible tablets directly into the liquid in proportion to the rate of liquid flowing past the tablets and the amount of tablets in contact with the surface of the tablets. Consequently, the use of a dispersal valve that directs only a portion of a fluid mixing stream through the trough permits a user to controllably dispense the dispersant in the trough at a substantially constant rate over an extended period of time. In addition, the use of a canister that continually funnels unspent dispersant into the trough permits one to controllably dispense material at a substantially constant rate for two weeks or longer.

FIG. 3 shows a perspective view of a prior art canister 130 having a hand grip ridge 131 with a finger recess 132 to permit a user to lift canister 130 out of a dispersal valve. Canister 130 comprises a housing having an upper region 133 and a lower region having a first fluid port 134 and a second fluid port 135. A cap 136 extends over ports 134 and 135 to seal the canister during storage. A break line 138 extends around each of the ports to permit cap 136 to be quickly separated from canister when the canister is in use. A mating line 137 identifies where the top half and the lower half of canister have been joined together to form a closed canister.

Figure 4:
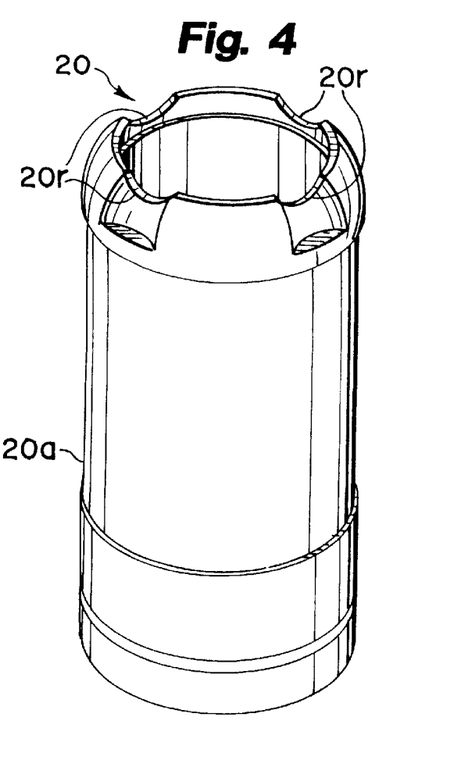

FIG. 4 shows a perspective view of an annular nestable canister 20 of the present invention for use in dispersal valve 10. Nestable canister 20 nests with a second nestable canister 40 (FIG. 6) to provide a multiple delivery or dispensing system. Nestable canister includes an outer cylindrical exterior 20a that enables canister 20 to be inserted into the existing dispersal valves in a manner that a single canister would be inserted. In addition, nestable canister 20 has a central area where a second nestable canister can be placed. Nestable canister 20 includes relief areas 20r to enable a person to grasp nestable canister 20 when it is within a dispersal valve. Nestable canister 20 is made from a rigid polymer plastic and normally stands in a upright position in a dispersal valve.

Figure 4A:
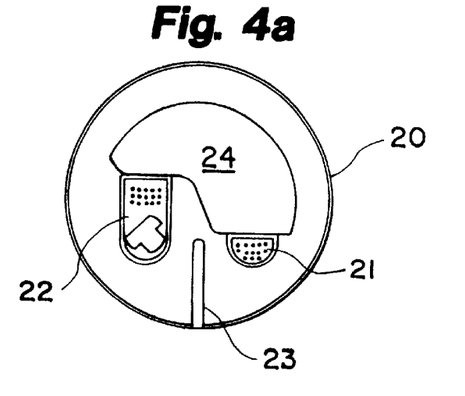

FIG. 4A shows a bottom view of a nestable canister 10 showing a radial extension 25 having a canister inlet 21 and a canister outlet 22. A slot 23 in canister 20 provides a key for ensuing that the canister is properly inserted into the dispersal valve that has a corresponding mating tab.

Figure 4B:
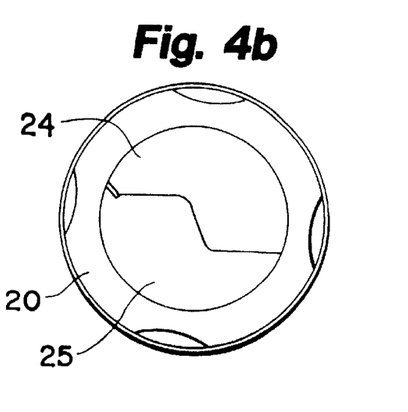

FIG. 4B shows a top view of canister 20 revealing the lower radial inward extension 25 that holds means for directing fluid in and out of canister 20. Radial inward extension 25 extends only partway across the bottom portion of canister 20 leaving a central opening in canister 20. Reference numeral 24 identifies the central opening 24 in nestable canister 20 to enable the nesting and operation of a second canister within canister 20.

Figure 5:
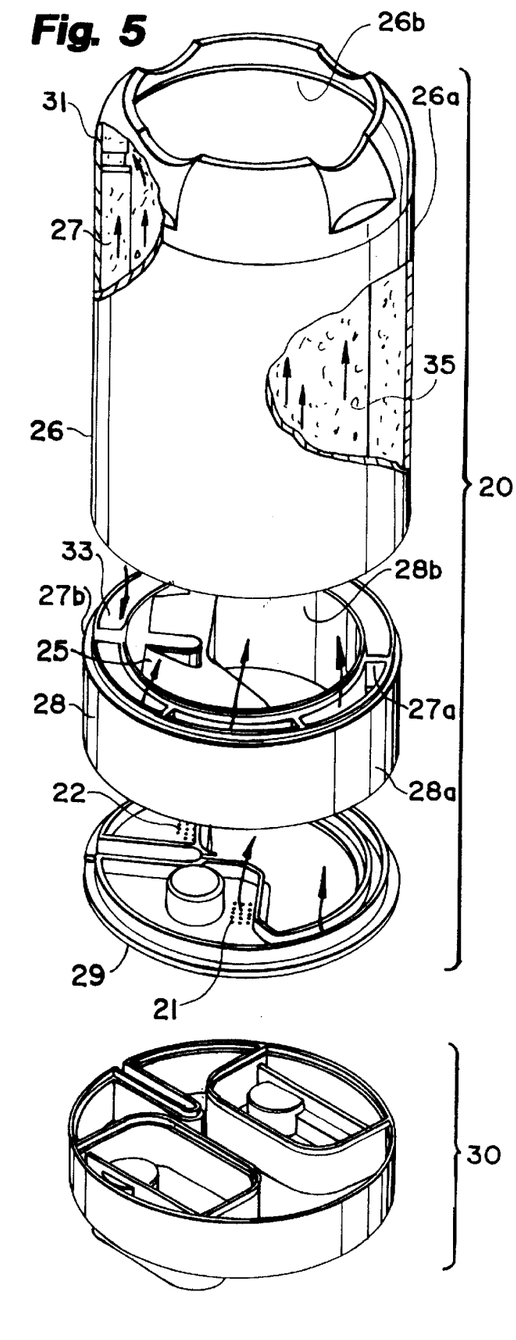

FIG. 5 shows an exploded cut-away view of nestable canister 20 and a manifold 30 that can be used to connect a set of nestable canister to an existing dispersal valve. Nestable canister 20 includes an upper cylindrical section 26 having an annular chamber defined by a cylindrical inner wall 26b and an outer cylindrical wall 26a. Located within the annular chamber defined by walls 26b and 26a is a longitudinal rib 27 that forms both a separator and spacer between inner wall 26b and outer wall 26a. Rib 27 extends upward from cylindrical base 28. The rib 27 terminates in the top portion of section 26 in the annular chamber 31 that extends around the top portion of cylindrical section 26.

Longitudinal rib 27 divides the space between walls 26b and 26a so that water from the inlet to canister 20 cannot flow directly to the outlet of the canister 20 but must pass through the water treatment minerals 31 in canister 20. The minerals for the water treatment are shown located between the inner wall 26b and outer wall 26a and are preferably a contact water treatment mineral 35 for removal of bacteria and algae from the water.

In the embodiment shown the water treatment mineral 35 is a bacteria and algae inhibiting mineral comprising zinc particles and zinc particles coated with silver which are dispersed within an acid absorber such as limestone which can absorbs acids generated within the dispenser. In the embodiment shown, the water treatment composition for killing bacteria and inhibiting algae growth in a recirculating water system comprises a plurality of zinc particles having a maximum dimension on the order of 1/8 of an inch with the zinc particle having an exterior irregular surface and a coating of silver located on the exterior irregular surface of the zinc particles. The silver is sufficiently thick so as to kill bacteria that comes into contact with the silver. In most applications the water treatment composition has a coating of silver which is about 1% of the weight of the silver coated zinc particle. In general, the water treatment composition of chemical dispersants used in canister 20 includes zinc particles having sufficiently small dimensions so that sufficient contact can be made with the silver on the zinc to provide effective killing of bacteria and algae. In addition to the silver coated zinc particles the composition includes uncoated zinc particles dispersed throughout the mixture of the dispersant composition in nestable canister 20 as the zinc particles prevent algae from growing. It is belived that the zinc ions from the canister enter the pool and kill algae in the pool. Thus the second canister provides in situ water treatment by killing bacteria that come into contact with the silver as well as the usual benefits of dispersion of materials into the water. With the use of a contact type bactericide in the second canister it allows the present invention to provide in situ killing of bacteria which makes it possible to lower the levels of chlorine used in the pools. That is, chlorine levels in the pool or spa do not need to be maintained at high levels as a portion of the bacteria killing can be done outside the pool or spa by the contact bactericide in the second canister. Thus the present invention provides a method for reducing the chlorine levels in a body of water without having to maintain the chlorine at high levels.

The canister 20 is unique in that minerals within the canister include an acid absorber with the acid absorber available for absorbing acids which are generated by the production of chlorine in another dispensing canister 40 (FIG. 6) located in the fluid system. Thus a dependent relationship exists between the two canisters with the canister 40 carrying materiel that absorbs undesirable by-products from the chemical dispersant in the first canister.

To illustrate the operation of nestable canister 20 reference should be made to FIG. 5 which shows base 28 and base plate 29 that sealably fasten to each other with the base 28 further sealably fastened to member 26. FIG. 5 shows that extension 25 extends only across the bottom portion of nestable container 20. Extension 25 has an internal passage (not shown) that directs fluid from inlet 21 vertically upward into half of an annular chamber defined on the ends by end longitudinal rib 27a and end longitudinal rib 27b and on the sides by the outer cylindrical member 28a and inner cylindrical member 28b. The three arrows extending upward from base 28 indicate the direction of incoming flow in nestable canister 20. That is, fluid enters inlet 21 and is directed by the passages in extension 25 into the half annular inlet chamber where the fluid travels upward though the dispersant as indicted by the arrows. Once the fluid reaches the top of canister 20 it flows over the end of longitudinal rib 27 and downward to the outlet in canister 20. In order for the fluid to be discharged from the nestable container the fluid must flow downward through additional mineral dispersant wherein it is discharged from the canister after it passes into extension 25 which through an internal passage (not shown) directs the fluid to outlet 22.

Thus in fluid operation of nestable canister 20 a portion of the fluid mixing stream from a dispersal valve 10 is directed through inlet 21 wherein it flows upward through the dispersant located in one side of nestable canister until the fluid reaches the top of canister 20. Once the fluid passes around rib 27 the fluid flows downward through a similar chamber containing additional dispersant until the fluid is discharged through outlet 22.

Located below nestable canister 20 is a manifold 30 for use in adapting the nestable canister for use in existing dispersal valves. In certain applications manifold 30 is not needed; however, in some applications the manifold can be used to allow a wide variety of nestable canisters to be used in various types of dispersal valves.

Figure 5A:
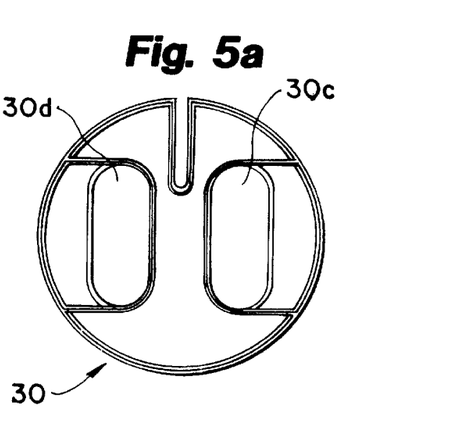
Figure 5B:
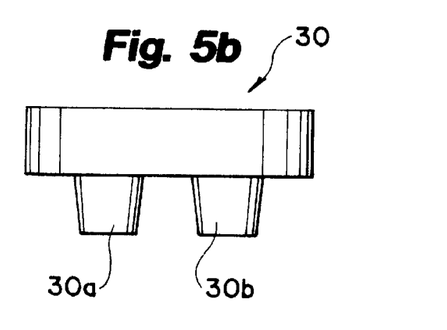

FIG. 5A shows a top view of manifold 30 and FIG. 5B show a side view of manifold 30 while FIG. 5 reveals the interior of manifold 30. Manifold 30 includes a first extension 30a for engaging an outlet port of a dispersal valve and a second extension 30b for engaging an inlet port of a dispersal valve. FIG. 5a shows that the top of manifold 30 includes an enlarged outlet 30c for engaging with inlets from two or more nestable canisters and an enlarged inlet 30d for engaging with outlets from two or more nestable canisters.

Figure 6:
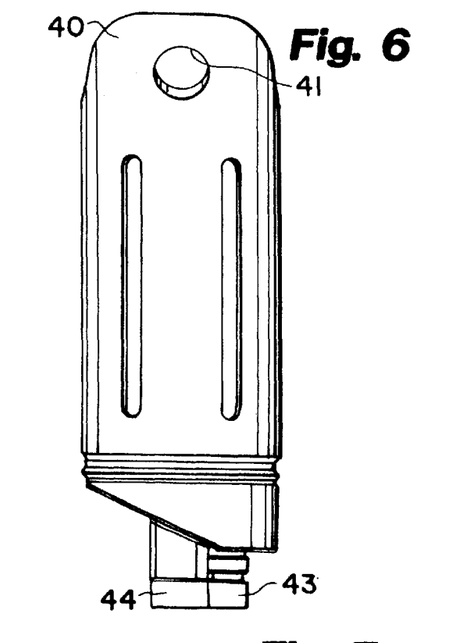
Figure 7:
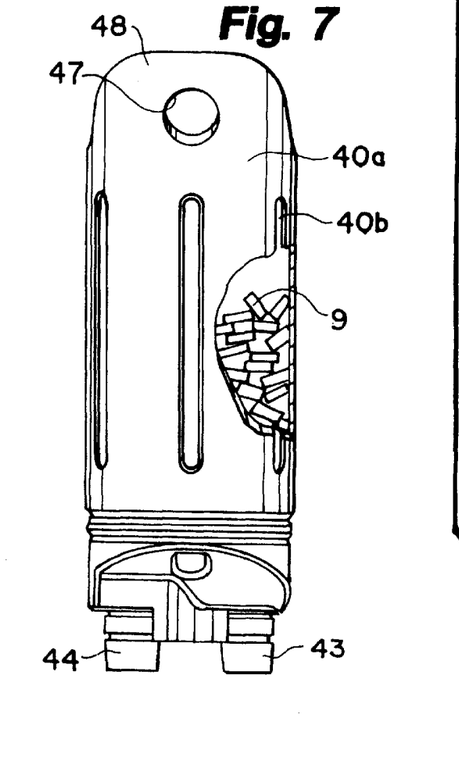

FIGS. 6 and 7 show a second nestable canister 40 therein. FIG. 6 shows a side view of nestable canister 40 and FIG. 7 shows a partial cutaway view of nestable canister 40. Nestable canister 40 comprises a cylindrical outer wall 40a with reinforcing groves 40b to provide stiffness to internally nestable canister 40. A first finger grip 41 and a second finger grip 42 enable the nestable canister 40 to be lifted from or lowered into the nestable canister 20. Nestable canister is preferably made from a polymer plastic or the like.

Figure 1:
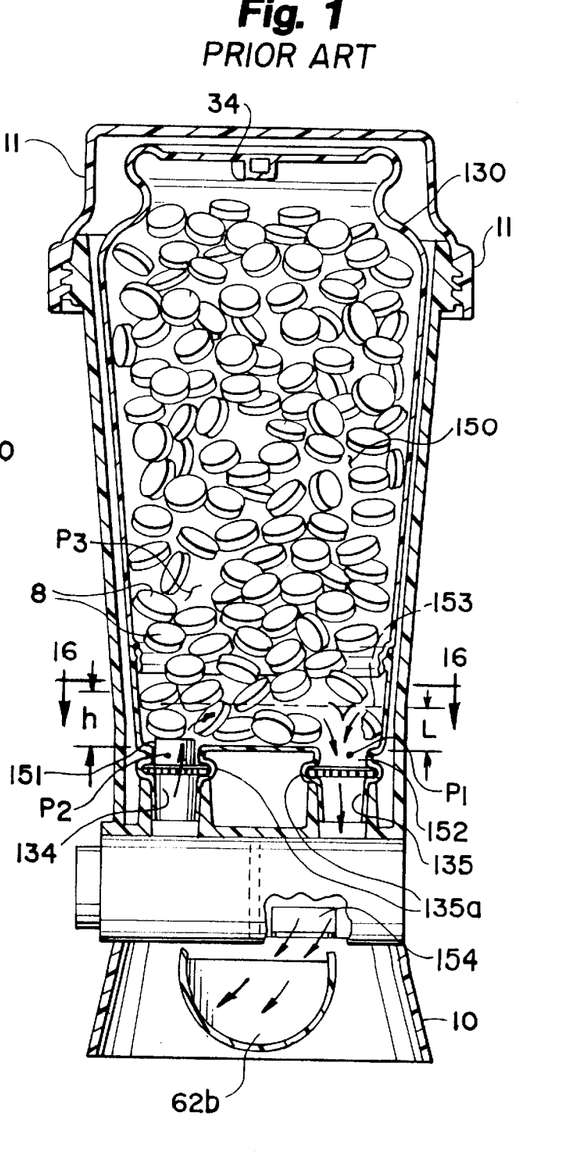
Figure 2:
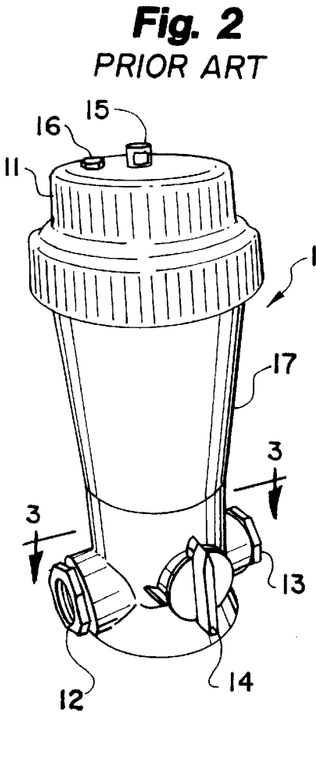
Figure 3:
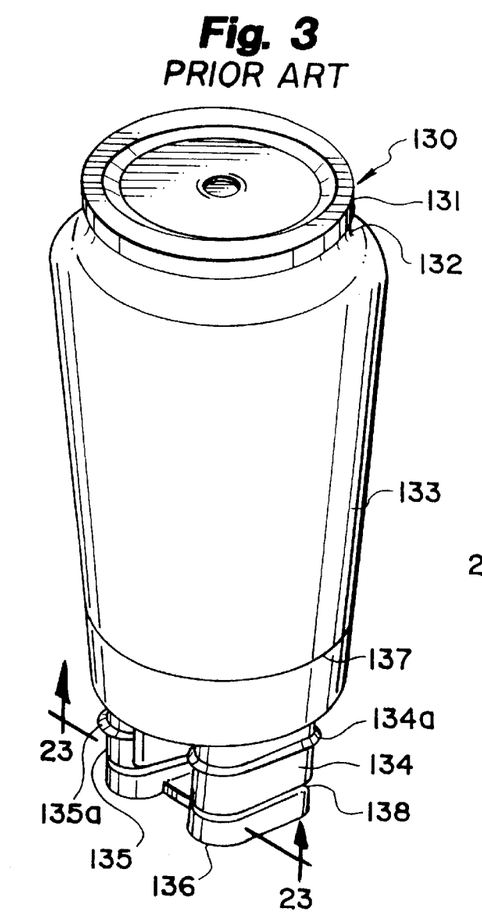

Nestable canister 40 includes an inlet port 43 for engaging a portion of the inlet flow from a dispersal valve and a fluid outlet port 44 for directing the portion of the fluid back into the main liquid stream. The cutaway view shows dispersant tablets 9 located within nestable canister 40. Tablets 9 can typically be chlorine tablets for killing bacteria. The operation of nestable canister 40 is similar to the operation of nestable canister 130 shown in FIG. 2 except that nestable canister 40 does not receive all the fluid mixing stream from valve inlet member 134. That is, the fluid mixing stream that flows through the dispersal valve is bifurcated so that a first portion of the incoming fluid mixing stream is diverted through the dispersant in nestable canister 40 and a second portion of the fluid mixing stream is directed through the nestable canister 20.

Figure 8:
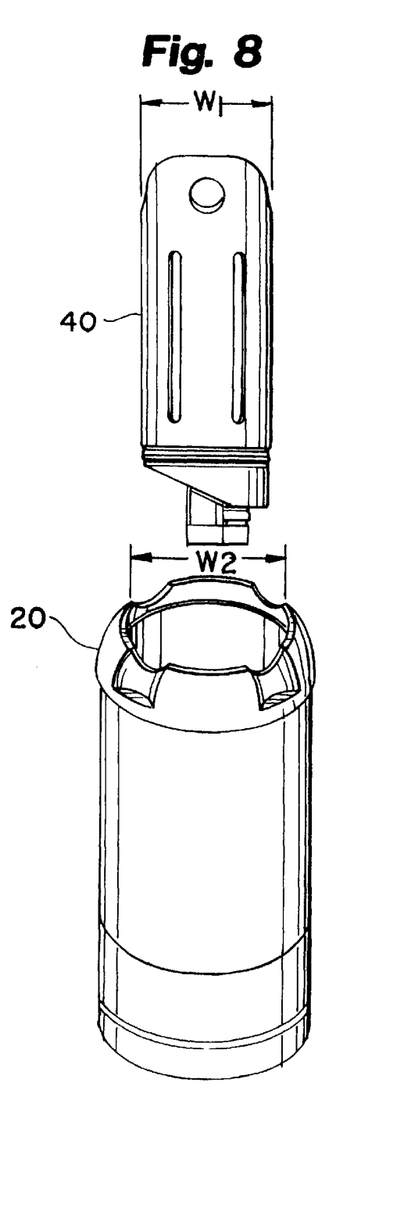

FIG. 8 is an exploded view illustrates that nestable canister 40 can be axially inserted within the nestable canister 20. Nestable canister 40 includes an outer dimension designated by $W_1$ and nestable canister 20 includes an inside dimension designated by $W_2$ with $W_2$ less than $W_1$ so that canister 40 can be freely inserted within the chamber formed by the interior of canister 20. FIG. 8 shows the two nestable canisters 40 and 20 prior to the insertion into a nesting relationship with each other.

Figure 9:
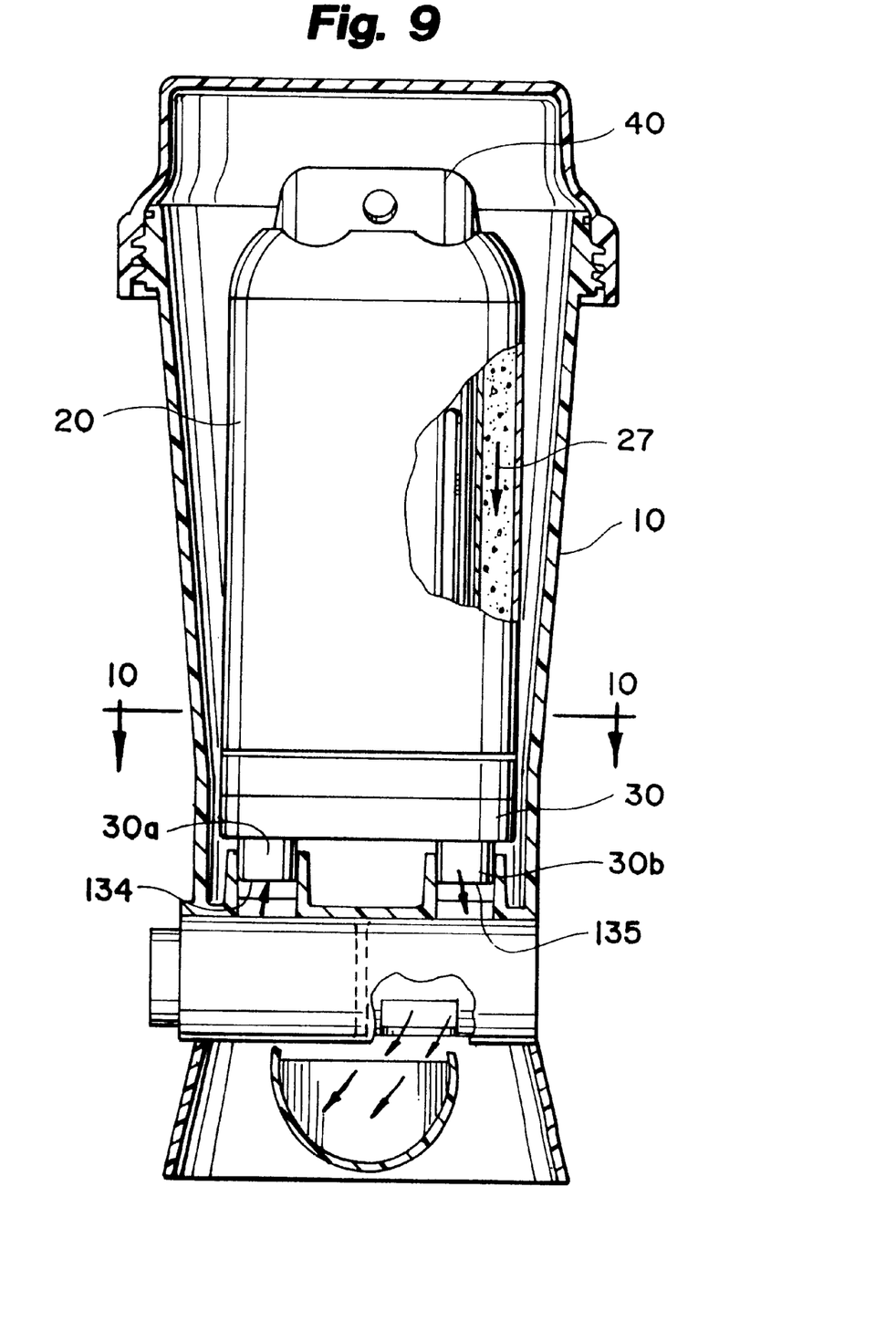

FIG. 9 shows a partial back cutaway view of dispersal valve 10 with nestable canister 20 and nestable canister 40 located in nesting relationship within the space formally occupied by canister 130. Manifold 30 directs a fluid mixing stream from valve inlet 134 into valve inlet 30a and manifold outlet 30b directs the fluid mixing stream together with the two dispersant back into the main liquid stream. The second nestable container is 40 shown nesting substantially within first nestable container 20.

Figure 10:
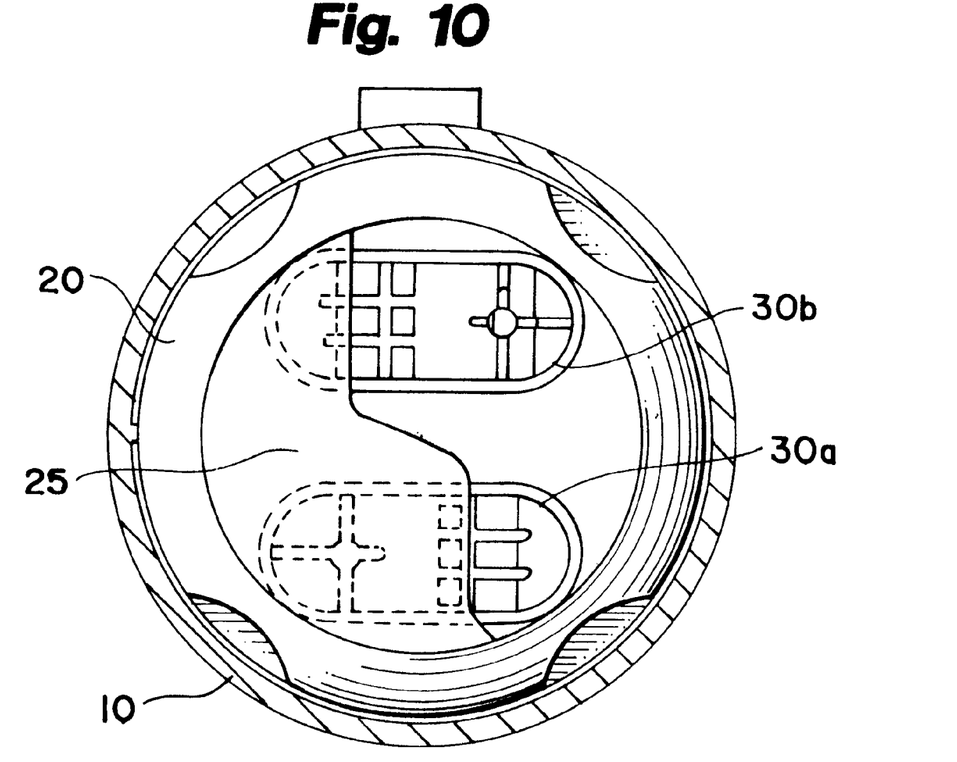

FIG. 10 shows a cross sectional view of canister 10 with the inner nestable canister 40 removed to show that nestable canister 20 extends over a portion of first manifold port 30a and second manifold port 30b. Thus there is a fluid path that provides for receiving a portion of the fluid mixing steam and allowing the portion of the fluid mixing stream to flow through the outer nestable canister 20. The remaining portion of the mixing fluid stream which is directed through the other portions of fluid ports 30a and 30b is directed through the second nestable canister which has inlets and outlets positioned to received and dispenses the other portion of the mixing fluid stream back into the dispersal valve. Thus the fluid mixing stream is bifurcated allowing portions of the bifurcated fluid mixing stream to be simultaneously but separately mixed with different chemical dispersants. After mixing of the chemical dispersant with the bifurcated fluid stream the two portions of the stream are combined in the dispersal valve before being directed back into the main liquid stream flowing through the dispersal valve.

Thus the present invention is a water treatment system that enables a person to dispense a single chemical dispersant or multiple chemical dispersants into the pool or spa by merely selecting the appropriate canisters for use in the dispersal valve to thereby provide a water treatment system for killing bacteria and algae in a recirculating water system. That is, with one canister including a first bacteria killing chemical such as a solid chlorine tablet or stick one can dispense chlorine into the recirculating water system to kill the bacteria in the water system and another canister, which includes a mineral having in situ bacteria-killing capabilities one can maintain the level of chlorine lower. Thus, one of the nestable containers contains a bactericide and the other nestable container contains an algaecide. That is, one can kill bacteria on contact by having a plurality of zinc particles having at least a partial coating of silver. In the embodiment shown the water treatment system is installed in a single compartment dispersal valve with the first canister and the second canister located in nesting relationship in the compartment of the dispersal valve. Not only can multiple chemical dispersants and minerals be dispensed into the system one can vary the dispensing rate by using a valve on the dispersal valve for varying the amount of water flowing through the dispersal valve. A further benefit of the invention is that the use of multiple nestable containers can be used to lower the amount of water circulated through the dispersant in the valve. For example, a normal setting of the dispersal valve with a single canister might deliver chemical dispersants at a rate of x per hour. With the present invention one of the multiple canisters might deliver chemical dispersants at a rate of 0.7x per hour. Thus the present invention allows the user to lower the dispersal rate by inserting a second canister to receive a portion of the mixing fluid stream in the dispersal valve. For example, the below table lists the output of a dispersal valve with a single canister containing chlorine tablets to a dispersal valve containing a set of nestable canisters one containing chlorine tablets and the other containing zinc particles, silver coated zinc particles and limestone.

| Dial Setting | Chlorine (oz/chlorine per hour) | Chlorine & Minerals (oz/chlorine per hour) |
| --- | --- | --- |
| 0 | .016 | .014 |
| 3 | .135 | .080 |
| 4.5 | .149 | .142 |
| 6 | .677 | .313 |
| 9 | 1.630 | .372 |

Thus a feature of the present invention is that the use of the nestable containers can be used to change the calibration of the valve to allow the dispersal valve to be used with different size bodies of water.

It is believed the silver metal surfaces are effective in killing bacteria due to the fact the bacterial cell walls contain various chemical groups that have an affinity for silver. When the bacteria cell wall comes in contact with the silver, the cell is strongly bound to the surface of the silver by the various chemical groups. The process alone helps prevent the bacteria from multiplying. However, in the presence of dissolved oxygen or very low levels of chlorine a further action can occur in which the various chemical groups react chemically with the surface of the silver to kill the bacteria by damaging or destroying the cell walls of the bacteria thus making the silver an ideal in situ killing material for use in the invention.

Zinc metal is believed to react in a similar manner, however, zinc is more effective in keeping the silver clean. That is, the bacteria on the silver surface combine with the zinc to produce a regenerated silver surface and zinc ions dissolved in water plus cell debris. The cell debris can be trapped on a filter in the mineral chamber. In the above example the minerals in the second canister comprised zinc (35.7 grams), silver-coated zinc (237 grams), and limestone (907.2 grams). The zinc acts as a carrier for the silver which is applied to the zinc in the form of a silver halide emulsion. The emulsion is applied in the form of paste and fixed through the use of a combination of heat, halogen light and a chemical developer. This fixing process converts the silver halide emulsion to silver which securely adheres to the zinc during the fixing process. The end result is a particle that has a complete coating of silver (about 1% silver to the weight of the zinc). The limestone at a nominal size of about ¼ of an inch. Thus the combination of a chlorine and silver and zinc dispersant composition is effective in killing bacteria and killing algae with the chlorine providing the fast killing action and the silver and zinc providing the long term killing action.

Figure 11:
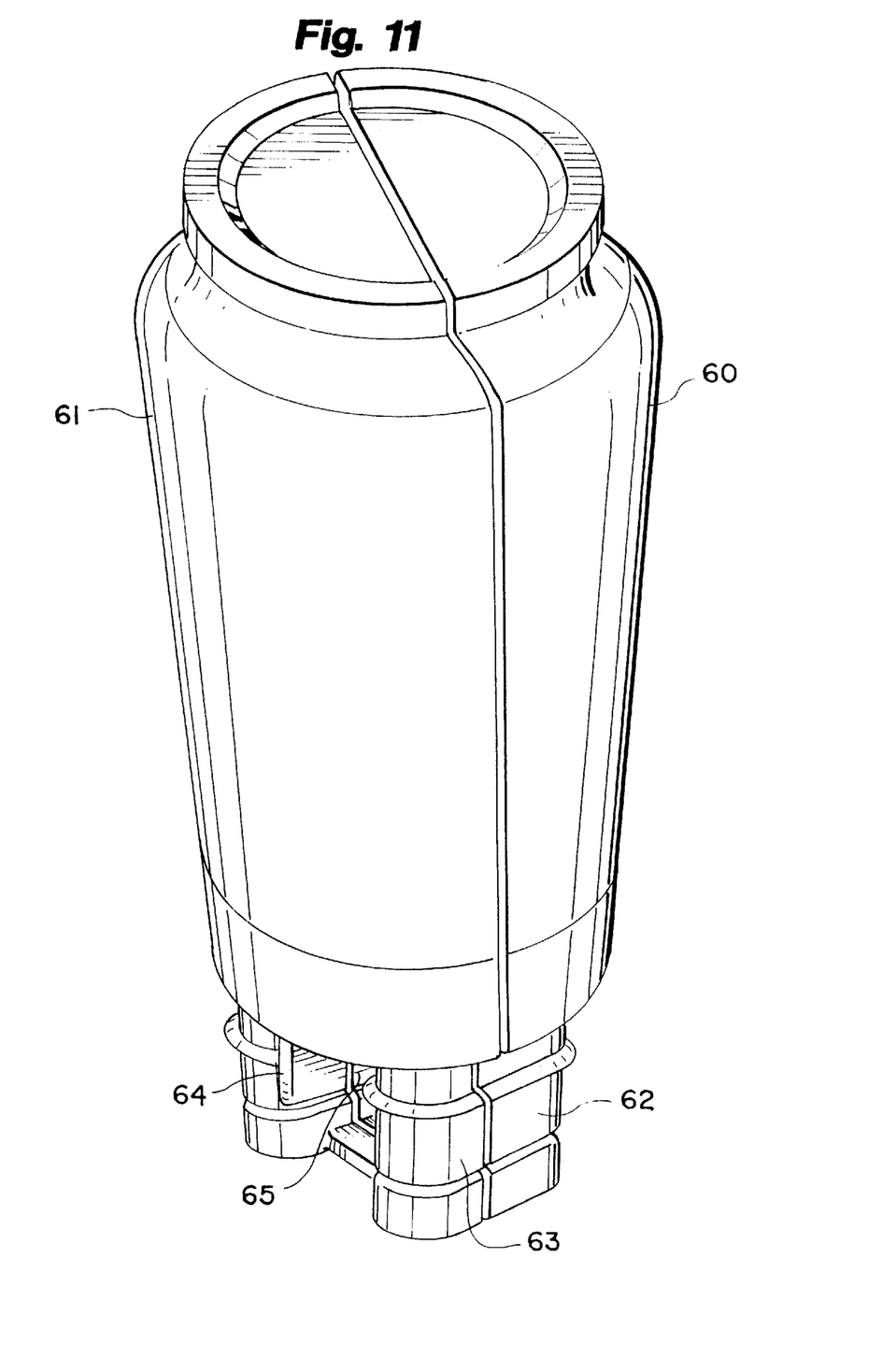

FIG. 11 shows an alternate embodiment of the invention wherein the nestable canister are formed into two longitudinally extending hemicylindrical canisters 60 and 61. Canisters 60 and 61 are separate canisters for holding the contents in isolation from each other. In the canisters 60 and 61 the fluid from the dispersal valve is split and is sent upward through the inlet ports 62 and 63 and through the respective canister where it is discharged through the outlet ports 65 and 64.

I claim:

1. A water treatment system for killing bacteria in situ and in a main body of water comprising:
   a first dispenser, said first dispenser including solid chlorine for dispensing chlorine into the water treatment system for killing bacteria, said first dispenser extending in a longitudinal direction in said water treatment system, said first dispenser having a top and a bottom and having an inlet and outlet thereto located on the bottom of said first dispenser;
   a second dispenser, said second dispenser separate from said first dispenser and extending longitudinally along said first dispenser to allow for removal of either said first dispenser or said second dispenser from said water treatment system, said second dispenser having a top and a bottom and having an inlet and outlet thereto located on the bottom of said second dispenser, said second dispenser holding a bacteria killing mineral therein for killing bacteria; and
   a first port for directing water from the main body of water into said first dispenser and into said second dispenser and a second port for directing water in the first dispenser and the second dispenser into the main body of water.

2. A dispenser for dispensing a bacteria killing composition into a water system comprising:
   a passage for directing a liquid stream into said dispenser;
   a compartment located in said dispenser;
   a dispenser inlet located in said dispenser for directing a liquid mixing stream into said compartment;
   a dispenser outlet located in said dispenser for directing the liquid mixing stream out of said compartment;
   a valve located in said dispenser for controlling the amount of water directed into the inlet located in said dispenser;
   a first nestable canister located in said compartment, said first nestable canister including a chamber therein for normally holding a solid water soluble chemical for killing bacteria in the water circulated through said canister, said canister having an inlet for bifurcating a liquid mixing stream from said dispenser inlet and an outlet for directing a bifurcated portion of the liquid mixing stream into said dispenser outlet; and
   a second nestable canister located in said compartment, said second nestable canister including a chamber therein for normally holding a second solid water soluble chemical for killing bacteria in the water circulated through said second nestable canister, said second canister having an inlet for receiving a further portion of the liquid mixing stream from said dispenser inlet and an outlet for directing the further portion of the liquid mixing stream into the dispenser outlet to cause the bifurcated liquid mixing stream to be combined before discharge from said dispenser.

3. A bactericide delivery system for use with different bactericides comprising;
   a first nestable canister, said first nestable canister having an open central interior and an annular chamber for holding a first bactericide therein, said first nestable canister including an inlet for directing a portion of a liquid mixing stream into the first nestable canister and an outlet for directing the portion of the liquid mixing stream back into the liquid;
   a second nestable canister, said second nestable canister located within the first nestable canister open central interior, said second nestable canister holding a bactericide different from said first bactericide with said second nestable canister having an inlet for direction a further portion of the liquid mixing stream into the second nestable canister and an outlet for directing the further portion of the liquid mixing stream out of the second nestable canister with said first inlet of said first nestable canister and said second canister positioned adjacent to each other so as to share the liquid mixing stream diverted toward said canisters to enable the liquid mixing stream to provide simultaneous but separate treatment of the liquid with two or more chemical materials.

4. The bactericide delivery system of claim 3 wherein said first nestable canister has a cylindrical exterior.

5. The bactericide delivery system of claim 3 wherein the nestable canisters are made from a polymer plastic.

6. The bactericide delivery system of claim 3 wherein the nestable canisters have a top and a bottom with the inlets and outlets thereto located on the bottom of said nestable canisters.

7. The bactericide delivery system of claim 3 wherein one of the nestable canisters contains a bactericide and the other nestable canister contains an algaecide.

8. The chemical dispersant apparatus of claim 2 wherein the first nestable canister includes limestone.

9. A water treatment system for killing bacteria in situ and in a main body of water comprising:
   a dispersal valve having a compartment therein, said dispersal valve having a removable cover;
   a dispenser located in said compartment of said dispersal valve, said dispenser including a first solid bacteria killing chemical, said dispersal valve dispensing a first liquid stream into said dispenser; and a further dispenser located in said dispersal valve, said further dispenser separate from said dispenser so that either said dispenser or said further dispenser can be replaced in said dispersal valve, said dispersal valve dispensing a second liquid stream into the further dispenser, said further dispenser holding a bacteria killing mineral therein for killing bacteria in the further dispenser, said further dispenser including an open central interior and an annular chamber for holding the bacteria killing mineral therein, said dispenser nested within the open central interior of said further dispenser, so that the further dispenser and the dispenser can simultaneously but separately kill bacteria with each of said dispenser or said further dispenser separately removable from the dispersal valve.

10. The water treatment system of claim 9 wherein the bacteria killing mineral in the further dispenser includes a carrier containing a silver coating and zinc particles.

11. The water treatment system of claim 9 wherein the dispenser and further dispenser each have a top and a bottom with each having an inlet and outlet thereto located on the bottom of said dispensers.

12. The water treatment system of claim 9 wherein one of the dispensers contains a bactericide and the other dispenser contains an algaecide.

13. The water treatment system of claim 9 wherein the bacteria killing material comprises a carrier having silver thereon.

14. The water treatment system of claim 13 wherein the bacteria killing material includes limestone for absorbing acids generated in said bacteria killing material.

15. The water treatment system of claim 9 wherein said dispersal valve has a single compartment that normally holds only a single dispersant;

said dispersal valve having a port for directing a first liquid stream into a dispenser for killing bacteria; and said further dispenser nested in said compartment of said dispersal valve, said further dispenser separate from said dispenser so that either said dispenser or said further dispenser can be separately removed from said dispersal valve.

16. A bactericide delivery system comprising:

a dispersal valve having a chamber therein, said dispersal valve having an opening with a removable cover for obtaining access to the chamber therein;

a liquid mixing stream, said liquid mixing stream flowing through the chamber;

a first nestable canister, said first nestable canister holding a first bactericide therein, said first nestable canister including an inlet for directing a portion of the liquid mixing stream into the first nestable canister and an outlet for directing the portion of the liquid mixing stream back into the liquid mixing stream, said first nestable canister having a top and a bottom with said inlet and said outlet located on the bottom of said first nestable canister, said first nestable canister located in the chamber of said dispersal valve; and a second nestable canister, said second nestable canister having an inlet for directing a further portion of the liquid mixing stream into the second nestable canister and an outlet for directing the further portion of the liquid mixing stream out of the second nestable canister, said second nestable canister having a top and a bottom with said inlet and said outlet located on the bottom of said second nestable canister, said second nestable canister located in the chamber of said dispersal valve with either of said first nestable canister or said second nestable canister replaceable by removal from the chamber through the opening in the dispersal valve.

* * * * *